United States Patent [19]

Eastlick

[11] 4,092,306
[45] May 30, 1978

[54] OXIDATION OF HYDRAZONES TO THE CORRESPONDING DIAZO COMPOUNDS IN THE PRESENCE OF A PHASE TRANSFER AND AN OXIDATION CATALYST WHICH IS IODINE, AN IODIDE OR AN IODONIUM SALT

[75] Inventor: David Thomas Eastlick, Lancaster, England

[73] Assignee: Glaxo Laboratories Limited, Greenford, England

[21] Appl. No.: 725,234

[22] Filed: Sep. 21, 1976

Related U.S. Application Data

[63] Continuation of Ser. No. 377,248, Jul. 9, 1973, abandoned.

[51] Int. Cl.$^2$ ............... C07C 113/00; C07C 113/02; C07C 113/04
[52] U.S. Cl. ..................... 260/141; 252/426; 252/441; 260/239 AA; 260/296 R; 260/329 AM; 260/347.7
[58] Field of Search ............ 260/141, 239 AA, 296 R, 260/329 AM, 347.7

[56] References Cited

PUBLICATIONS

Morrison et al., J. Org. Chem., vol. 26, pp. 2617 and 2618 (1961).
Theilheimer (I), "Synthetic Methods of Organic Chemistry," vol. 19, p. 155, #354 (1965).
Stark et al., Chemical Abstracts, vol. 72, p. 292, Item #11527t (1970).
Day et al., Chemical Abstracts, vol. 64, 9577d (1966).
Nenitzescu, "Organic Synteses," collected vol. II, pp. 496 and 497 (1943).
Smith, "Open–Chain–Nitrogen Compounds," vol. 2, pp. 165 and 166 (1966).
Smith et al., "Organic Syntheses," collective vol. III, pp. 351 and 352 (1955).
Theilheimer (II), "Synthetic Method of Organic Chemistry," vol. 16, p. 172, #360 (1962).

*Primary Examiner*—Floyd D. Higel
*Attorney, Agent, or Firm*—Bacon & Thomas

[57] ABSTRACT

A process for the preparation of diazo compounds, particularly diazo alkanes, is described in which a hydrazone is oxidized to a corresponding diazo compound in a two phase reaction medium in the presence of a phase transfer catalyst, and an oxidation catalyst which is iodine, and iodide or an iodonium salt, preferably in the presence of a base.

18 Claims, No Drawings

OXIDATION OF HYDRAZONES TO THE CORRESPONDING DIAZO COMPOUNDS IN THE PRESENCE OF A PHASE TRANSFER AND AN OXIDATION CATALYST WHICH IS IODINE, AN IODIDE OR AN IODONIUM SALT

This is a continuation of application Ser. No. 377,248, filed July 9, 1973, now abandoned.

This invention relates to a process for the preparation of diazo compounds.

There is a growing need for efficient esterification processes which can be applied to sensitive organic acids without disturbing their molecular geometry, i.e. without molecular disruption or molecular rearrangements such as isomerization and racemization. Such processes are particularly needed in the manufacture of cephalosporin and penicillin antibiotics where it is frequently necessary to protect a carboxyl group by esterification to enable chemical transformations to be carried out elsewhere in the molecule.

One class of esterifying agents which has been found particularly useful in the treatment of sensitive organic acids comprises diazoalkanes, in particular diazomethane and substituted diazomethanes, which react with the acid to give the methyl or substituted methyl ester respectively, often in near-stoichiometric yield. Although such esterifying agents are widely employed on a laboratory scale, the lack of a commercially acceptable method of preparing appropriate diazoalkanes has prevented their use in industrial scale esterification processes.

The most commonly used current methods of preparing diazo compounds such as diazoalkanes comprise the treatment of N-alkyl-N-nitroso ureas and sulphonamides with base and the oxidation of aldehydic and ketonic hydrazones with oxidising agents such as mercuric oxide, manganese dioxide, nickel peroxide, silver oxide and lead tetraacetate. The former method is disadvantageous in that the N-nitroso compounds employed are frequently unstable and difficult to store and in several cases exhibit carcinogenic properties. The oxidative preparations are preferred in that relatively stable, accessible materials are involved, but suffer the disadvantage that the oxidising agents are expensive and in most cases require careful preparation to ensure that they exhibit reproducible activity. Also, in some cases undesirably large quantities of the oxidising agent are required.

Since in addition to exhibiting useful esterifying properties diazoalkanes are valuable alkylating agents there is a need for a convenient and efficient process for their preparation. I have now found that diazo compounds such as diazo alkanes can be prepared by treatment of hydrazones with certain commercially acceptable oxidising agents in the presence of a phase transfer catalyst and a base, or, when the oxidation reaction is effected at low temperatures, followed by treatment with a base.

Thus according to one aspect of the invention I provide a process for the preparation of a diazo compound which comprises reacting the corresponding hydrazone with an oxidising agent in a reaction medium comprising water and a water-immiscible organic solvent in the presence of a phase transfer catalyst and, preferably, a base.

The diazo compound may be of the formula

(where $R^1$ is a hydrogen atom or an organic group having for example up to 20 carbon atoms, and $R^2$ is an organic group such as just defined; or where $R^1$ and $R^2$ together with the intervening carbon atom form a cyclic organic group having up to 15 carbon atoms, such as a cyclic hydrocarbon group which may be interrupted by one or more of O or N). The hydrazone will thus be of the formula

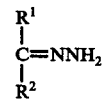

The oxidising agent is preferably an organic peracid, a hypohalite acid, a hypohalite salt or ester, chlorine, bromine or chromic acid, but other oxidising agents capable of oxidising hydrazones to diazo compounds may be used, e.g. potassium permanganate.

The oxidising agent may for example be an organic peracid such as peracetic acid or m-chloroperbenzoic acid; or a hypohalous acid or salt or ester thereof such as hypochlorous acid, sodium hypochlorite or t-butylhypochlorite. When the oxidation is effected by a halogen, this may for example be molecular chlorine or bromine; chlorine or bromine may also be used in an activated form, as in compounds which possess a source of positive halogen ions, such as an N-haloamide (e.g. an N-chloroamide such as N-chlorosuccinimide) or an N-halosulphonamide (e.g. an N-chloroarylsulphonamide such as chloroamine-T or N-chlorosaccharin). Mixtures of the oxidising agents may also be used to advantage, e.g. a combination of a peracid and an N-bromoamide.

If desired peracids may be formed in situ (e.g. from hydrogen peroxide and hexafluoroacetone).

The use of a phase transfer catalyst is particularly, advantageous, as regards the yield of the product, where the oxidising agent is a peracid, an N-haloamide or an N-halosulphonamide.

Peracetic acid is a particularly preferred oxidising agent for use in the process.

The reaction is preferably effected in the presence of an oxidation catalyst, particularly when the oxidising agent is an organic peracid. Such catalysts may for example be iodine or an iodide (e.g. ammonium iodide or a quaternary ammonium iodide) or an iodonium salt such as iodine bromide, a quinone (e.g. a benzoquinone such as tetrachlorobenzoquinone) or a metal cation (e.g. copper I or II, cobalt II or III, nickel II or manganese II, III or IV). The use of iodine or an iodide is particularly preferred in that advantageously higher yields of the desired diazo compound can be obtained.

The reaction is conveniently effected in an organic solvent, which is advantageously inert. Mixtures of solvents may also be used. Suitable solvents include chlorinated hydrocarbons, e.g. chloroform, 1,2-dichloroethane or methylene chloride; aromatic hydrocarbons, e.g. toluene or tetraline; aliphatic hydrocarbons, e.g. n-hexane or cyclohexane; and aliphatic and cyclic ethers, e.g. diethyl ether or tetrahydrofuran.

Suitable phase transfer catalysts are quaternary ammonium hydroxides or salts (e.g. such as tetra-n-butylammonium hydroxide, tri-n-octyl-n-propylammonium chloride); so-called crown ether [e.g. 2,5,8,15,18,21-hexaoxatricyclo (20.4.0.0.$^{9,14}$) hexacosane]; or phosphonium salts (e.g. alkyl phosphonium salts such as hexadecyltri-butylphosphonium bromide). Such phase transfer catalysts apparently assist the interphase transfer of the reagents, thus accelerating reaction rates. An oxidation catalyst, preferably iodine or an iodide, is desirably present in these circumstances.

The hydrazone (II) need not be completely dissolved in the solvent, although lower reaction rates may result if a significant proportion of the compound is out of solution. In such cases it may be convenient to mill crystals of the hydrazone to a fine particle size (e.g. c.10$\mu$) before oxidation in order to increase the reaction rate.

Both inorganic and organic bases may be used in the process; the base is preferably inert to the oxidising reaction conditions, but it need not necessarily be inert provided that the oxidation product of the base is itself capable of oxidising the hydrazone (II), preferably without loss of efficiency. Thus, for example, aqueous sodium hydroxide may be used as base together with chlorine as oxidising agent, since the resulting sodium hypochlorite will itself oxidise the hydrazone. Excess base should normally be employed in such circumstances to allow for consumption of base by the oxidising agent.

In general, inorganic bases which may be used include alkali metal and alkaline earth metal hydroxides, bicarbonates and carbonates, e.g. sodium or potassium hydroxide, bicarbonate or carbonate, or calcium carbonate. The use of an inorganic base is generally preferred for economic considerations.

Organic bases for use in the process are desirably substantially inert to the oxidising conditions, since such bases will generally not react to give a further oxidising species. Thus suitable organic bases include guanidines such as tetramethylguanidine, quaternary ammonium hydroxides such as tetra-n-butylammonium hydroxide, basic amides such as dimethylacetamide or resins with non-oxidisable basic groups e.g. quaternary ammonium resins, either in hydroxide or salt (e.g. cabonate) form.

It is usually convenient to use a water-soluble organic base which can be removed after the oxidation by aqueous washing.

It will be appreciated that when the oxidising agent is itself a base (e.g. cloramine-T) the presence of an additional base may be unnecessary.

The oxidation reaction is exothermic and may for example be effected at a temperature in the range $-50°$ to $+100°$ C, preferably $-15°$ to $+30°$ C. The temperature will to some extent depend on the nature of the hydrazone employed.

The course of the reaction may be followed using infra-red spectroscopy, e.g. by monitoring the strong absorption in the region 2030–2080 cm$^{-1}$ characteristic of diazoalkanes. Alternatively, ultraviolet spectroscopy may be employed, and is particularly suitable in many cases for the quantitative determination of the yield of diazo compound. In some cases it is possible to follow the course of the reaction using thin layer chromatography, a technique which is valuable in assessing whether any unreacted hydrazone is present. The amount of diazo compound produced can also be determined by acidification and measurement of the amount of nitrogen evolved.

The process is conveniently carried out by adding the oxidising agent to a mixture of the hydrazone (II) and the base and catalyst(s) in solution or suspension in the medium, the rate of addition of the oxidising agent and the thermal control preferably being such as to maintain the temperature of the reaction mixture in the range $-50°$ to $+100°$ C. Other modes of addition may also be employed, however, thus, for example, the base and the oxidising agent may be added simultaneously and equivalently to a solution of the hydrazone. Alternatively, the base and the oxidising agent may be pre-mixed, preferably at low temperature, and added to a solution or suspension of the hydrazone the catalyst(s). Where the various components are brought together in organic solvents it is preferred that the solvents should be the same.

The reaction is conveniently effected using 0.5–2.0, e.g. 0.9–1.5, moles of oxidising agent and 0.5–10, e.g. 0.9–5.0, moles of base per mole of hydrazone. Generally the preferred range is 1.0 to 1.4 moles of oxidising agent and sufficient base to neutralise all the acid present or produced. When a water/water-immiscible organic solvent system is used it is advantageous to add base simultaneously and equivalently with the oxidising agent so as to maintain a pH of about 10.

When an oxidation catalyst is used, the required level is generally very low, usually from $10^{-1}$ to $10^{-6}$, preferably from $10^{-2}$ to $10^{-4}$ moles per mole hydrazone. The level of phase transfer catalyst required is generally from 0.1% to 5% by weight of the hydrazone, preferably 1 to 2%. Higher levels of phase transfer catalyst may be used but are undesirable on economic grounds.

A wide range of hydrazones may be employed in the process, these being prepared by, for example, standard methods starting from aldehydes and ketones, e.g. reaction of a compound R$^1$R$^2$CO (where R$^1$ and R$^2$ have the above-defined meanings) with hydrazine. Thus in the above formulae I and II R$^1$ and/or R$^2$ may be alkyl groups preferably containing 1–6 carbon atoms, such as methyl, ethyl, n-propyl, isopropyl etc.; cycloalkyl groups which may contain 5–7 carbon atoms in the ring, e.g. cyclopentyl, cyclohexyl; aryl groups such as phenyl, naphthyl etc.; aralkyl groups, which are preferably monocyclic and contain 1–6 carbon atoms in the alkyl portion, such as benzyl; 5- or 6- membered heterocyclic rings containing one or more atoms of O, N and S, e.g. 2-thienyl, 2-furyl, 2-pyridinyl etc.; heterocyclic-substituted alkyl groups, preferably containing 1–6 carbon atoms in the alkyl portion, e.g. 2-thienylmethyl, 2-furylmethyl etc.; or any of the above groups substituted by one or more halogen atoms, cyano, nitro, alkyl, alkylsulphonyl or alkoxy groups, these last preferably containing 1–6 carbon atoms, such as methyl, ethyl, n-propyl, isopropyl, ethoxy, isopropoxy or methylsulphonyl. The hydrazones may also possess a further hydrazone group. The aralkyl, alkyl, cycloalkyl and heterocyclic group may be unsaturated.

Alternatively R$^1$ and R$^2$ may, together with the attached carbon atoms form a cyclic structure, e.g. cyclopentyl, cyclohexyl, 9-fluorenyl, pyranyl or piperidinyl.

As indicated above, the diazo compounds prepared by the process of the invention are useful agents for the esterification of sensitive organic acids and may, for example, be used to introduce easily removable ester groups into compounds such as penicillins and cephalosporins. Compounds of formula I useful for this purpose include those in which $R^1$ and $R^2$ are such that the resulting ester grouping $R^1R^2CH-$ is an aralkyl group containing 1 or 2 carbocyclic or heterocyclic aryl groups attached to the C 1 atom of a lower ($C_{1-6}$) alkyl portion, e.g. benzyl, diphenylmethyl, 2-furylmethyl, di(2-thienyl) methyl, phenyl(2-thienyl) methyl or 9-fluorenyl; a cycloalkyl group such as cyclopentyl; or a substituted version of any of these groups, e.g. p-nitrobenzyl or di(p-methoxyphenyl) methyl. This list is not however, intended to be exhaustive.

it is believed that the presence of base enhances the yield of diazo compound by binding any acids present in or produced by the oxidising agent which would otherwise tend to react with the diazo compound leading to its decomposition. The base is also thought to moderate the oxidation reaction, reducing any tendency for the diazo compound to be oxidised further to, for example, corresponding carbonyl derivatives.

In certain cases, e.g. when low reaction temperatures, such as in the range $-50°$ to $-20°$ C, are employed to moderate the reaction rate, it may be possible to dispense with the presence of the base during oxidation of the hydrazone, base being added subsequently to stabilise the diazo product. Such modified reaction procedures comprise a further feature of the invention.

The following Examples serve to illustrate the invention.

Temperatures are in ° C.

EXAMPLE 1

Diphenyldiazomethane

To benzophenone hydrazone (19.6 g, 0.1 mole) in water (50 ml) and dichloromethane (100 ml) at 0° was added tetrabutylammonium hydroxide solution (1.89 ml, 40% solution). The pH was adjusted to 10 with glacial acetic acid and iodine (4 ml, 1% w/v solution) added. To the stirred solutions was added peracetic acid solution (17.8 ml, 1.0 × 0.1 moles) at 0° over 15 minutes, the pH being controlled to near 10 by the simultaneous addition of sodium hydroxide solution. After the addition the two phase system was stirred for 30 minutes at 0° and the separated organic layer washed with water (2 × 250 ml). A UV assay at 525 nm of a suitably diluted aliquot corresponded to a yield of 78.6% of the diazoalkane.

EXAMPLE 2

Diphenyldiazomethane

The method and experimental quantities are exactly those of Example I except that ethyl acetate was substituted as the organic solvent. A UV assay at 525 nm of a suitably diluted aliquot corresponded to a yield of 64.2% of diazoalkane.

EXAMPLE 3

Diphenylidiazomethane

To benzophenone hydrazone (19 6 g, 0.1 mole) in dichloromethane (100 ml) and water (50 ml) was added trioctylpropylammonium chloride (1.26 g, 2.92 m. moles) and iodine (4 ml, 1% w/v solution). To this stirred system was added peracetic acid solution (17.8 ml, 1.0 × 0.1 moles) at 0° over 15 minutes the pH being controlled to near 10 by the simultaneous addition of sodium hydroxide solution. After stirring for an additional 30 minutes at 0° the red organic layer was washed with water (1 × 150 ml, 2 × 250 ml). A UV assay at 525 nm of a suitably diluted aliquot corresponded to a yield of 84.9% of the diazoalkane.

In a similar way goods yields of diphenyldiazomethane were obtained by substituting tetrabutylammonium chloride, tetrabutylammonium iodide, benzyltriethylammonium chloride, dodecyltrimethylammonium chloride and benzyltrimethylammonium hydroxide for trioctylpropylammonium chloride.

EXAMPLE 4

Diphenyldiazomethane

In this Example the method and experimental quantities are identical to Example 1 except that dilute ammonia solution was substituted for sodium hydroxide to control the pH to near 10. A UV assay at 525 nm of a suitably diluted aliquot corresponded to a yield of 71.1% of the diazoalkane.

EXAMPLE 5

Diphenyldiazomethane

To benzophenone hydrazone (19.6 g, 0.1 mole) in water (100 ml) and dichloromethane (100 ml) was added tetrabutylammonium hydroxide (1.89 ml, 40% solution) followed by iodine (4 ml, 1% w/v solution). The pH was adjusted to 10 with glacial acetic acid and then potassium permanganate solution (10.54 g, 0.067 moles) added over 15 minutes at 20°. The solution was stirred for a further 30 minutes, filtered from the precipitated manganese dioxide and the separated organic layer washed with water (3 × 250 ml). A UV assay at 525 nm of a suitably diluted aliquot corresponded to a yield of 27.8% of the diazoalkane.

EXAMPLE 6

Diphenyldiazomethane

To benzophenone hydrazone (19.6 g, 0.1 mole) stirred in dichloromethane (100 ml) and water (100 ml) was added tetrabutylammonium hydroxide (2 ml) and the pH adjusted to 6 with acid. Hexafluoroacetone (15 g, 0.135 moles) was added as a dichloromethane solution at C°, followed by 30% hydrogen peroxide (3.75 g, 1.1 × 0.1 mole) the pH adjusted to 8 and a small crystal of iodine added. The system was stirred for 1½ hours while the temperature was allowed to rise towards ambient. The separated organic layer was washed with water (2 × 100 ml) and a UV assay at 525 nm on a suitably diluted aliquot corresponded to a yield of 47.5% diazoalkane.

EXAMPLE 7

Diphenyldiazomethane

Benzophenone hydrazone (19.6 g, 0.1 moles) in dichloromethane (100 ml) water (50 ml), tetrabutylammonium hydroxide solution (4.0 ml) and iodine (4 ml, 1% w/v solution) were all brought to pH 7 – 8 by the addition of acid. A solution of chloroamine T (28.2 g, 0.1 mole) in water (220 ml) was added to the stirred mixture over 30 minutes and the red solution then washed with water (2 × 200 ml). A UV assay on a suitably diluted aliquot corresponded to a yield of 69.7% diazoalkane.

I claim:

1. A process for the preparation of a diazo compound of the formula:

where $R^1$ is selected from the group consisting of hydrogen and R, where R is selected from the group consisting of phenyl, naphthyl, benzyl, thienyl, furyl, pyridinyl, thienylmethyl, furylmethyl, $C_{1-6}$ alkenyl, $C_{5-7}$ cycloalkenyl, $C_{1-6}$ alkyl, and $C_{5-7}$ cycloalkyl groups and such groups substituted by at least one of chloro, bromo, cyano, nitro, $C_{1-6}$ alkyl, $C_{1-6}$ alkylsulphonyl, and $C_{1-6}$ alkoxy; $R^2$ has independently any of the defined meanings for R; or where $R_1$ and $R_2$ together with the intervening carbon atom form a member selected from the group consisting of cyclopentyl, cyclohexyl, fluorenyl, pyranyl and piperidinyl which comprises reacting a hydrazone of the formula:

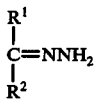

where $R^1$ and $R^2$ are as defined above, with 0.5-2.0 moles per mole of hydrazone of an oxidising agent in the presence of 0.5-10 moles of base per mole of hydrazone, an oxidation catalyst and a phase transfer catalyst in a two phase reaction medium, said base being an alkali metal or alkaline earth metal hydroxide, bicarbonate or carbonate, a guanidine, a basic amide or a quaternary ammonium hydroxide, said oxidising agent being a member selected from the group consisting of a peracid, an N-haloamide or an N-halosulphonamide or mixtures thereof, and said phase transfer catalyst being selected from the group consisting of tetra-n-butyl ammonium hydroxide, tri-n-octyl-n-propylammonium chloride, 2, 5, 8, 15, 18, 21-hexaoxatricyclo (20.4.0.0.$^{19,14}$) hexacosane, hexadecyltri-butylphosphonium bromide, tetrabutylammonium-chloride or -iodide, benzyltriethyl ammonium chloride, dodecyltrimethyl ammonium chloride and benzyltrimethyl ammonium hydroxide, said oxidation catalyst being a member selected from the group consisting of iodine, an iodide and an iodenium salt.

2. A process as claimed in claim 1 wherein the phase transfer catalyst is present in an amount of 1 to 2% by weight of the hydrazone.

3. A process as claimed in claim 1, wherein the $R^1R^2C$— group is a benzyl, diphenylmethyl, 2-furylmethyl, di(2-thienyl)methyl, phenyl (2-thienyl)methyl, 9-fluorenyl, p-nitrobenzyl or di(p-methoxyphenyl)-methyl group.

4. A process as claimed in claim 1 wherein the oxidising agent is peracetic acid.

5. A process as claimed in claim 1 which is effected at a temperature of $-15°$ to $+30°$ C.

6. A process as claimed in claim 1 wherein the base is an alkali metal or alkaline earth metal hydroxide, bicarbonate or carbonate.

7. A process as claimed in claim 6 wherein the base is sodium or potassium hydroxide, bicarbonate or carbonate, or calcium carbonate.

8. A process as claimed in claim 1 wherein the base is a guanidine, a basic amide or a quaternary ammonium hydroxide.

9. A process as claimed in claim 8 wherein the base is tetramethylguanadine, dimethylacetamide and tetra-n-butyl ammonium hydroxide.

10. A process as claimed in claim 1 wherein the two phase reaction medium is water and a water immiscible organic solvent.

11. A process as claimed in claim 10 wherein the organic solvent is chloroform, 1,2-dichloroethane, methylene chloride, toluene, tetralin, N-hexane, cyclohexane, diethyl ether, tetrahydrofuran or ethyl acetate.

12. A process as claimed in claim 11 wherein the iodide is ammonium iodide or a quaternary ammonium iodide.

13. A process as defined in claim 1 wherein the oxidising agent is a peracid, N-chlorosuccinimide or chloramine-T.

14. A process as claimed in claim 1 wherein the oxidation catalyst is ammonium iodide, quaternary ammonium iodide or iodine bromide.

15. A process as claimed in claim 10 wherein the oxidation catalyst is iodine or an iodide.

16. A process as claimed in claim 1 wherein the oxidation catalyst is present in an amount of from $10^{-2}$ to $10^{-4}$ moles per mole of hydrazone.

17. A process for the preparation of a diazo compound of the formula:

where $R^1$ is selected from the group consisting of hydrogen and R, where R is selected from the group consisting of phenyl, naphthyl, benzyl, thienyl, furyl, pyridinyl, thienylmethyl, furylmethyl, $C_{1-6}$ alkenyl, $C_{5-7}$ cycloalkenyl, $C_{1-6}$ alkyl, and $C_{5-7}$ cycloalkyl groups and such groups substituted by at least one of chloro, bromo, cyano, nitro, $C_{1-6}$ alkyl, $C_{1-6}$ alkylsulphonyl and $C_{1-6}$ alkoxy; $R^2$ has independently any of the defined meanings for R; or where $R^1$ and $R^2$ together with the intervening carbon atom form a member selected from the group consisting of cyclopentyl, cyclohexyl, fluorenyl, pyranyl and piperidinyl which comprises reacting a hydrazone of the formula:

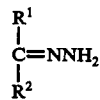

where $R^1$ and $R^2$ are as defined above, with 0.5-2.0 moles per mole of hydrazone of an oxidising agent in the presence of an oxidation catalyst and a phase transfer catalyst in a two phase reaction medium at a temperature of from $-50°$ C to $-20°$ C, said oxidising agent being a member selected from the group consisting of a peracid, an N-haloamide or an N-halosulphonamide or mixtures thereof, and said phase transfer catalyst being selected from the group consisting of tetra-n-butyl ammonium hydroxide, tri-n-octyl-n-propylammonium chloride, 2, 5, 8, 15, 18, 21-hexaoxatricyclo (20.4.0.0.$^{9,14}$) hexacosane, hexadecyltri-butyl-phosphonium bromide, tetrabutylammonium-chloride or -iodide, benzyltriethyl ammonium chloride, dodecyltrimethyl ammonium chloride and benzyltrimethyl ammonium hydroxide, said oxidation catalyst being a member selected from the group consisting of iodine, an iodide and an iodonium salt, followed by the addition of from 1.5–10 moles of base per mole of hydrazone, said base being an alkali metal or alkaline earth metal hydroxide, bicarbonate or carbonate, a guanidine, a basic amide or a quaternary ammonium hydroxide to stabilize the diazo product.

18. A process as claimed in claim 17 wherein the oxidation catalyst is present in an amount of from $10^{-2}$ to $10^{-4}$ moles per mole of hydrazone.

* * * * *